(12) United States Patent
Oral et al.

(10) Patent No.: US 7,993,333 B2
(45) Date of Patent: Aug. 9, 2011

(54) ABLATION CATHETERS

(75) Inventors: Hakan Oral, Ann Arbor, MI (US); Fred Morady, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 1013 days.

(21) Appl. No.: 11/159,055

(22) Filed: Jun. 22, 2005

(65) Prior Publication Data

US 2005/0240176 A1 Oct. 27, 2005

Related U.S. Application Data

(62) Division of application No. 10/280,653, filed on Oct. 25, 2002, now abandoned.

(51) Int. Cl.
*A61B 18/14* (2006.01)
(52) U.S. Cl. ............................ 606/41; 607/122; 600/374
(58) Field of Classification Search ................... 606/41, 606/48–50; 600/374; 607/101, 102, 116, 607/122
See application file for complete search history.

(56) References Cited

U.S. PATENT DOCUMENTS

| | | | |
|---|---|---|---|
| 3,516,412 A | 6/1970 | Ackerman | |
| 4,411,266 A | 10/1983 | Cosman | |
| 4,432,377 A | 2/1984 | Dickhudt | |
| 4,660,571 A * | 4/1987 | Hess et al. | 607/116 |
| 4,699,147 A * | 10/1987 | Chilson et al. | 600/374 |
| 4,785,815 A | 11/1988 | Cohen | |
| 4,860,769 A | 8/1989 | Fogarty et al. | |
| 4,869,248 A | 9/1989 | Narula | |
| 4,882,777 A | 11/1989 | Narula | |
| 4,896,671 A | 1/1990 | Cunningham et al. | |
| 4,920,980 A | 5/1990 | Jackowski | |
| 4,940,064 A * | 7/1990 | Desai | 607/122 |
| 4,966,597 A | 10/1990 | Cosman | |
| 5,010,894 A | 4/1991 | Edhag | |
| 5,016,808 A | 5/1991 | Heil, Jr. et al. | |
| 5,083,565 A | 1/1992 | Parins et al. | |
| 5,100,423 A | 3/1992 | Fearnot | |
| 5,156,151 A | 10/1992 | Imran | |
| 5,215,103 A | 6/1993 | Desai | |
| 5,228,442 A | 7/1993 | Imran et al. | |
| 5,231,995 A | 8/1993 | Desai | |
| 5,239,999 A | 8/1993 | Imran | |
| 5,255,679 A | 10/1993 | Imran | |
| 5,279,299 A | 1/1994 | Imran | |

(Continued)

FOREIGN PATENT DOCUMENTS

AU 5200671 10/2005

(Continued)

OTHER PUBLICATIONS

EP Search Report, EP Application No. 03 777 928.7 dated Nov. 21, 2007.

(Continued)

*Primary Examiner* — Michael Peffley
(74) *Attorney, Agent, or Firm* — Casmir Jones SC

(57) ABSTRACT

The present invention relates generally to multifunctional catheters for performing ablation procedures, and more particularly to ablation catheters utilized in the treatment of atrial fibrillation and other cardiac disorders. The present invention eliminates many of the problems associated with previous ablation catheters by providing an ablation treatment not dependent upon continuous lesions.

66 Claims, 11 Drawing Sheets

Catheter 2

3 sided tip with 2 section coil

U.S. PATENT DOCUMENTS

| | | | |
|---|---|---|---|
| 5,281,218 A | 1/1994 | Imran | |
| 5,313,943 A * | 5/1994 | Houser et al. | 600/374 |
| 5,324,284 A | 6/1994 | Imran et al. | |
| 5,327,889 A | 7/1994 | Imran | |
| 5,330,466 A | 7/1994 | Imran | |
| 5,342,295 A | 8/1994 | Imran | |
| 5,345,936 A | 9/1994 | Pomeranz et al. | |
| 5,364,352 A | 11/1994 | Cimino et al. | |
| 5,365,926 A | 11/1994 | Desai | |
| 5,383,917 A * | 1/1995 | Desai et al. | 607/102 |
| 5,391,147 A | 2/1995 | Imran et al. | |
| 5,397,339 A | 3/1995 | Desai | |
| 5,400,783 A | 3/1995 | Pomeranz et al. | |
| 5,404,638 A | 4/1995 | Imran | |
| 5,406,946 A | 4/1995 | Imran et al. | |
| 5,411,025 A * | 5/1995 | Webster, Jr. | 600/374 |
| 5,423,808 A | 6/1995 | Edwards | |
| 5,433,198 A | 7/1995 | Desai | |
| 5,445,148 A | 8/1995 | Jaraczewski et al. | |
| 5,462,545 A | 10/1995 | Wang et al. | |
| 5,465,717 A | 11/1995 | Imran et al. | |
| 5,471,982 A | 12/1995 | Edwards | |
| 5,487,757 A | 1/1996 | Truckai et al. | |
| 5,492,119 A | 2/1996 | Abrams | |
| 5,500,011 A | 3/1996 | Desai | |
| 5,507,802 A | 4/1996 | Imran | |
| 5,509,411 A | 4/1996 | Littmann et al. | |
| 5,527,279 A | 6/1996 | Imran | |
| 5,533,967 A | 7/1996 | Imran | |
| 5,545,193 A | 8/1996 | Fleischman et al. | |
| 5,545,200 A | 8/1996 | West et al. | |
| 5,558,073 A * | 9/1996 | Pomeranz et al. | 600/374 |
| 5,575,766 A | 11/1996 | Swartz et al. | |
| 5,575,810 A | 11/1996 | Swanson et al. | |
| 5,578,007 A | 11/1996 | Imran et al. | |
| 5,582,609 A | 12/1996 | Swanson et al. | |
| 5,588,964 A | 12/1996 | Imran et al. | |
| 5,595,183 A | 1/1997 | Swanson et al. | |
| 5,596,995 A | 1/1997 | Sherman et al. | |
| 5,598,848 A | 2/1997 | Swanson et al. | |
| 5,607,462 A | 3/1997 | Imran | |
| 5,620,481 A | 4/1997 | Desai et al. | |
| 5,637,090 A | 6/1997 | McGee et al. | |
| 5,645,064 A | 7/1997 | Littmann et al. | |
| 5,645,082 A | 7/1997 | Sung et al. | |
| 5,656,029 A | 8/1997 | Imran et al. | |
| 5,657,755 A | 8/1997 | Desai | |
| 5,662,606 A | 9/1997 | Cimino et al. | |
| 5,666,970 A | 9/1997 | Smith | |
| 5,680,860 A | 10/1997 | Imran | |
| 5,681,280 A | 10/1997 | Rusk et al. | |
| 5,682,885 A | 11/1997 | Littmann et al. | |
| 5,685,322 A | 11/1997 | Sung et al. | |
| 5,687,723 A | 11/1997 | Avitall | |
| 5,693,078 A | 12/1997 | Desai et al. | |
| 5,697,928 A | 12/1997 | Walcott et al. | |
| 5,699,796 A | 12/1997 | Littmann et al. | |
| 5,706,809 A | 1/1998 | Littmann et al. | |
| 5,711,298 A | 1/1998 | Littmann et al. | |
| 5,722,975 A | 3/1998 | Edwards et al. | |
| 5,741,320 A | 4/1998 | Thornton et al. | |
| 5,766,152 A | 6/1998 | Morley et al. | |
| 5,775,327 A | 7/1998 | Randolph et al. | |
| 5,782,760 A | 7/1998 | Schaer | |
| 5,782,828 A | 7/1998 | Chen et al. | |
| 5,800,482 A | 9/1998 | Pomeranz et al. | |
| 5,810,740 A | 9/1998 | Paisner | |
| 5,827,272 A | 10/1998 | Breining et al. | |
| 5,837,001 A | 11/1998 | Mackey | |
| 5,849,028 A | 12/1998 | Chen | |
| 5,857,464 A | 1/1999 | Desai | |
| 5,857,997 A | 1/1999 | Cimino et al. | |
| 5,860,920 A | 1/1999 | McGee et al. | |
| 5,863,291 A | 1/1999 | Schaer | |
| 5,871,523 A | 2/1999 | Fleischman et al. | |
| 5,873,865 A | 2/1999 | Horzewski et al. | |
| 5,876,399 A | 3/1999 | Chia et al. | |
| 5,881,732 A | 3/1999 | Sung et al. | |
| 5,882,333 A | 3/1999 | Schaer et al. | |
| 5,885,278 A | 3/1999 | Fleischman | |
| 5,891,027 A | 4/1999 | Tu et al. | |
| 5,891,135 A | 4/1999 | Jackson et al. | |
| 5,891,137 A | 4/1999 | Chia et al. | |
| 5,893,847 A | 4/1999 | Kordis | |
| 5,893,884 A | 4/1999 | Tu | |
| 5,895,355 A | 4/1999 | Schaer | |
| 5,895,417 A | 4/1999 | Pomeranz et al. | |
| 5,897,554 A | 4/1999 | Chia et al. | |
| 5,904,680 A | 5/1999 | Kordis et al. | |
| 5,906,605 A | 5/1999 | Coxum | |
| 5,910,129 A | 6/1999 | Koblish et al. | |
| 5,911,720 A | 6/1999 | Bourne et al. | |
| 5,916,214 A | 6/1999 | Cosio et al. | |
| 5,928,191 A | 7/1999 | Houser et al. | |
| 5,931,835 A | 8/1999 | Mackey | |
| 5,935,063 A | 8/1999 | Nguyen | |
| 5,938,694 A | 8/1999 | Jaraczewski et al. | |
| 5,951,471 A | 9/1999 | De la Rama et al. | |
| 5,954,719 A | 9/1999 | Chen et al. | |
| 5,957,842 A | 9/1999 | Littmann et al. | |
| 5,960,796 A | 10/1999 | Sung et al. | |
| 5,967,978 A | 10/1999 | Littmann et al. | |
| 5,971,980 A | 10/1999 | Sherman | |
| 5,992,418 A | 11/1999 | de la Rama et al. | |
| 5,997,532 A | 12/1999 | McLaughlin et al. | |
| 6,001,093 A | 12/1999 | Swanson et al. | |
| 6,001,095 A | 12/1999 | De la Rama et al. | |
| 6,002,956 A | 12/1999 | Schaer | |
| 6,021,340 A | 2/2000 | Randolph et al. | |
| 6,029,091 A | 2/2000 | De la Rama et al. | |
| 6,042,580 A | 3/2000 | Simpson | |
| 6,045,550 A | 4/2000 | Simpson et al. | |
| 6,048,329 A | 4/2000 | Thompson et al. | |
| 6,049,737 A | 4/2000 | Simpson et al. | |
| 6,052,612 A | 4/2000 | Desai | |
| 6,059,778 A | 5/2000 | Sherman | |
| 6,063,077 A | 5/2000 | Schaer | |
| 6,068,629 A | 5/2000 | Haissaguerre et al. | |
| 6,070,094 A | 5/2000 | Swanson et al. | |
| 6,071,274 A | 6/2000 | Thompson et al. | |
| 6,071,279 A | 6/2000 | Whayne et al. | |
| 6,071,282 A * | 6/2000 | Fleischman | 606/41 |
| 6,074,351 A | 6/2000 | Houser et al. | |
| 6,086,581 A | 7/2000 | Reynolds et al. | |
| 6,088,610 A | 7/2000 | Littmann et al. | |
| 6,096,036 A | 8/2000 | Bowe et al. | |
| 6,099,524 A | 8/2000 | Lipson et al. | |
| 6,106,522 A | 8/2000 | Fleischman et al. | |
| 6,119,041 A | 9/2000 | Pomeranz et al. | |
| 6,129,724 A | 10/2000 | Fleischman et al. | |
| 6,141,576 A | 10/2000 | Littmann et al. | |
| 6,146,379 A | 11/2000 | Fleischman | |
| 6,165,169 A | 12/2000 | Panescu | |
| 6,167,291 A | 12/2000 | Barajas et al. | |
| 6,171,306 B1 | 1/2001 | Swanson et al. | |
| 6,200,314 B1 | 3/2001 | Sherman et al. | |
| 6,214,002 B1 | 4/2001 | Fleischman et al. | |
| 6,216,043 B1 | 4/2001 | Swanson et al. | |
| 6,216,044 B1 | 4/2001 | Kordis | |
| 6,231,570 B1 | 5/2001 | Tu | |
| 6,238,390 B1 | 5/2001 | Tu et al. | |
| 6,241,666 B1 | 6/2001 | Pomeranz et al. | |
| 6,241,724 B1 | 6/2001 | Fleischman et al. | |
| 6,241,726 B1 | 6/2001 | Chia et al. | |
| 6,241,727 B1 | 6/2001 | Tu et al. | |
| 6,241,754 B1 | 6/2001 | Swanson et al. | |
| 6,245,067 B1 | 6/2001 | Tu et al. | |
| 6,251,107 B1 | 6/2001 | Schaer | |
| 6,256,540 B1 | 7/2001 | Panescu et al. | |
| 6,258,087 B1 | 7/2001 | Edwards | |
| 6,264,664 B1 | 7/2001 | Aveilanet | |
| 6,267,746 B1 | 7/2001 | Bumbalough | |
| 6,290,697 B1 | 9/2001 | Tu et al. | |
| 6,293,943 B1 | 9/2001 | Panescu et al. | |
| 6,302,880 B1 | 10/2001 | Schaer | |
| 6,309,385 B1 | 10/2001 | Simpson | |
| 6,332,880 B1 | 12/2001 | Yang et al. | |

| | | |
|---|---|---|
| 6,332,881 B1 | 12/2001 | Carner et al. |
| 6,346,104 B2 | 2/2002 | Daly et al. |
| 6,353,751 B1 | 3/2002 | Swanson et al. |
| 6,360,128 B2 | 3/2002 | Kordis et al. |
| 6,371,955 B1 | 4/2002 | Fuimaono et al. |
| 6,379,352 B1 | 4/2002 | Reynolds et al. |
| 6,391,024 B1 | 5/2002 | Sun et al. |
| 6,428,536 B2 | 8/2002 | Panescu et al. |
| 6,447,506 B1 | 9/2002 | Swanson et al. |
| 6,454,758 B1 | 9/2002 | Thompson et al. |
| 6,456,864 B1 | 9/2002 | Swanson et al. |
| 6,460,545 B2 | 10/2002 | Kordis |
| 6,471,699 B1 | 10/2002 | Fleischman et al. |
| 6,475,213 B1 | 11/2002 | Whayne et al. |
| 6,475,214 B1 | 11/2002 | Moaddeb |
| 6,477,396 B1 | 11/2002 | Mest et al. |
| 6,488,678 B2 | 12/2002 | Sherman et al. |
| 6,500,172 B1 | 12/2002 | Panescu |
| 6,514,246 B1 | 2/2003 | Swanson et al. |
| 6,522,905 B2 | 2/2003 | Desai |
| 6,529,756 B1 | 3/2003 | Phan |
| 6,540,744 B2 | 4/2003 | Hassett et al. |
| 6,544,262 B2 | 4/2003 | Fleischman |
| 6,554,794 B1 | 4/2003 | Mueller et al. |
| 6,558,378 B2 | 5/2003 | Sherman et al. |
| 6,572,612 B2 | 6/2003 | Stewart et al. |
| 6,574,492 B1 | 6/2003 | Ben-Haim et al. |
| 6,575,997 B1 | 6/2003 | Palmer et al. |
| 6,607,505 B1 | 8/2003 | Thompson et al. |
| 6,607,520 B2 | 8/2003 | Keane |
| 6,625,482 B1 | 9/2003 | Panescu et al. |
| 6,628,976 B1 | 9/2003 | Fuimaono et al. |
| 6,632,223 B1 | 10/2003 | Keane |
| 6,635,056 B2 | 10/2003 | Kadhiresan et al. |
| 6,638,275 B1 | 10/2003 | McGaffigan et al. |
| 6,640,120 B1 | 10/2003 | Swanson et al. |
| 6,652,513 B2 | 11/2003 | Panescu et al. |
| 6,658,279 B2 | 12/2003 | Swanson et al. |
| 6,669,693 B2 * | 12/2003 | Friedman ................ 606/41 |
| 6,701,180 B1 | 3/2004 | Desai |
| 6,702,811 B2 | 3/2004 | Stewart et al. |
| 6,730,078 B2 | 5/2004 | Simpson et al. |
| 6,738,673 B2 | 5/2004 | Desai |
| 6,746,446 B1 | 6/2004 | Hill et al. |
| 6,752,804 B2 | 6/2004 | Simpson et al. |
| 6,761,716 B2 | 7/2004 | Kadhiresan et al. |
| 6,805,131 B2 | 10/2004 | Kordis |
| 6,813,520 B2 | 11/2004 | Truckai et al. |
| 6,814,732 B2 | 11/2004 | Schaer |
| 6,830,576 B2 | 12/2004 | Fleischman et al. |
| 6,893,438 B2 | 5/2005 | Hall et al. |
| 6,893,439 B2 | 5/2005 | Fleischman |
| 6,961,602 B2 | 11/2005 | Fuimaono et al. |
| 6,966,908 B2 | 11/2005 | Maguire et al. |
| 6,972,016 B2 | 12/2005 | Hill et al. |
| 7,025,766 B2 | 4/2006 | Whayne et al. |
| 7,029,471 B2 | 4/2006 | Thompson et al. |
| 7,047,068 B2 | 5/2006 | Haissaguerre |
| 7,048,734 B1 | 5/2006 | Fleischman et al. |
| 7,099,712 B2 | 8/2006 | Fuimaono et al. |
| 7,115,122 B1 | 10/2006 | Swanson et al. |
| 7,151,964 B2 | 12/2006 | Desai |
| 7,155,270 B2 | 12/2006 | Solis et al. |
| 7,163,537 B2 | 1/2007 | Lee et al. |
| 2001/0008967 A1 | 7/2001 | Sherman |
| 2001/0018608 A1 | 8/2001 | Panescu et al. |
| 2001/0020166 A1 | 9/2001 | Daly et al. |
| 2001/0039418 A1 | 11/2001 | Schaer et al. |
| 2001/0051803 A1 | 12/2001 | Desai et al. |
| 2002/0010392 A1 | 1/2002 | Desai |
| 2002/0065465 A1 | 5/2002 | Panescu et al. |
| 2002/0120263 A1 | 8/2002 | Brown et al. |
| 2002/0128643 A1 | 9/2002 | Simpson et al. |
| 2002/0161361 A1 | 10/2002 | Sherman et al. |
| 2002/0161422 A1 | 10/2002 | Swanson et al. |
| 2002/0165532 A1 | 11/2002 | Hill et al. |
| 2002/0198522 A1 | 12/2002 | Kordis |
| 2003/0055419 A1 | 3/2003 | Panescu et al. |
| 2003/0055420 A1 | 3/2003 | Kadhiresan et al. |
| 2003/0060865 A1 | 3/2003 | Desai |
| 2003/0093069 A1 | 5/2003 | Panescu et al. |
| 2003/0181819 A1 | 9/2003 | Desai |
| 2003/0199862 A1 | 10/2003 | Simpson et al. |
| 2003/0199868 A1 | 10/2003 | Desai et al. |
| 2003/0204186 A1 | 10/2003 | Geistert |
| 2004/0116921 A1 | 6/2004 | Sherman |
| 2004/0152980 A1 | 8/2004 | Desai |
| 2005/0015084 A1 | 1/2005 | Hill et al. |
| 2005/0065512 A1 | 3/2005 | Schaer et al. |
| 2005/0148892 A1 | 7/2005 | Desai |
| 2005/0177146 A1 | 8/2005 | Sherman |
| 2005/0234444 A1 | 10/2005 | Hooven |
| 2006/0089637 A1 * | 4/2006 | Werneth et al. ................ 606/41 |
| 2006/0106375 A1 | 5/2006 | Sherman et al. |
| 2006/0111700 A1 * | 5/2006 | Kunis et al. .................... 606/41 |
| 2006/0111708 A1 | 5/2006 | Vanney et al. |
| 2006/0189975 A1 | 8/2006 | Whayne et al. |
| 2006/0206109 A1 | 9/2006 | Swanson |
| 2006/0241366 A1 | 10/2006 | Falwell et al. |
| 2007/0027448 A1 | 2/2007 | Paul et al. |
| 2007/0083195 A1 | 4/2007 | Werneth et al. |

FOREIGN PATENT DOCUMENTS

| | | |
|---|---|---|
| CA | 2328064 | 8/1943 |
| CA | 2371935 | 3/1945 |
| CA | 2136988 | 10/1994 |
| CA | 2512216 | 10/2003 |
| CA | 2276755 C | 5/2006 |
| CA | 2251041 C | 6/2006 |
| EP | 0428812 B1 | 3/1995 |
| EP | 0598742 B1 | 8/1999 |
| EP | 0957794 B1 | 11/1999 |
| EP | 0879016 B1 | 10/2003 |
| EP | 1384445 B1 | 2/2006 |
| EP | 1011437 B1 | 5/2006 |
| EP | 1207798 B1 | 6/2006 |
| EP | 1321166 B1 | 7/2006 |
| EP | 1343427 B1 | 7/2006 |
| EP | 1690564 A1 | 8/2006 |
| EP | 0828451 B1 | 9/2006 |
| EP | 1014874 B1 | 12/2006 |
| EP | 1455667 B1 | 1/2007 |
| JP | 2002-505140 | 9/1999 |
| WO | WO 90/06079 | 6/1990 |
| WO | WO 93/25273 | 12/1993 |
| WO | WO 94/12098 | 6/1994 |
| WO | WO 96/10961 | 4/1996 |
| WO | WO 96/32885 | 10/1996 |
| WO | WO 96/32897 | 10/1996 |
| WO | WO 96/34558 | 11/1996 |
| WO | WO 96/34559 | 11/1996 |
| WO | WO 96/34560 | 11/1996 |
| WO | WO 96/34567 | 11/1996 |
| WO | WO 96/34570 | 11/1996 |
| WO | WO 96/34650 | 11/1996 |
| WO | WO 96/34652 | 11/1996 |
| WO | WO 96/34653 | 11/1996 |
| WO | WO 97/17893 | 5/1997 |
| WO | WO 97/17904 | 5/1997 |
| WO | WO 97/15919 | 7/1997 |
| WO | WO 97/25917 | 7/1997 |
| WO | WO 97/32525 | 9/1997 |
| WO | WO 97/36541 | 10/1997 |
| WO | WO 97/40760 | 11/1997 |
| WO | WO 97/42996 | 11/1997 |
| WO | WO 98/18520 | 5/1998 |
| WO | WO 98/19611 | 5/1998 |
| WO | WO 98/26724 | 6/1998 |
| WO | WO 99/56649 | 11/1999 |
| WO | WO 02/060523 | 8/2002 |
| WO | 03/089997 | 10/2003 |
| WO | 2004/037072 | 5/2004 |
| WO | WO 2005/065562 | 7/2005 |
| WO | WO 2005/065563 | 7/2005 |
| WO | WO 2005/104972 | 11/2005 |
| WO | WO 2006/017517 | 2/2006 |
| WO | WO 2006/044794 | 4/2006 |
| WO | WO 2006/049970 | 5/2006 |

| WO | WO 2006/052651 | 5/2006 |
| WO | WO 2006/052906 | 5/2006 |
| WO | WO 2007/016123 | 2/2007 |
| WO | WO 2007/024785 | 3/2007 |

OTHER PUBLICATIONS

EP Search Report, EP Application No. 03 777 928.7 dated Jun. 18, 2008.

International Search Report, PCT/US05/20845, dated Sep. 21, 2005.

International Search Report, PCT/US2003/034091, dated Jul. 16, 2004.

JP Patent Application No. 2004-547216, Sep. 14, 2009 Office Action.

Canadian Office Action dated Dec. 15, 2010, Canadian Patent Application No. 2,570,207.

* cited by examiner

Catheter 2 Prototype: 5 sided tip with 2 section coil

Catheter 2

3 sided tip with 2 section coil

ABLATION CATHETERS

This application is a divisional application of co-pending U.S. patent application Ser. No. 10/280,653, filed Oct. 25, 2002.

FIELD OF THE INVENTION

The present invention relates generally to catheters for performing targeted tissue ablation in a subject. In particular, the present invention provides devices comprising wire tipped and umbrella tipped ablation catheters, and methods for treating conditions (e.g., cardiac arrhythmias) with these devices.

BACKGROUND OF THE INVENTION

Mammalian organ function typically occurs through the transmission of electrical impulses from one tissue to another. A disturbance of such electrical transmission may lead to organ malfunction. One particular area where electrical impulse transmission is critical for proper organ function is in the heart. Normal sinus rhythm of the heart begins with the sinus node generating an electrical impulse that is propagated uniformly across the right and left atria to the atrioventricular node. The atrioventricular node in return causes the atria contract. Atrial contraction leads to the pumping of blood into the ventricles in a manner synchronous with the pulse.

Atrial fibrillation refers to a type of cardiac arrhythmia where there is disorganized electrical conduction in the atria causing rapid uncoordinated contractions which result in ineffective pumping of blood into the ventricle and a lack of synchrony. During atrial fibrillation, the atrioventricular node receives electrical impulses from numerous locations throughout the atria instead of only from the sinus node. This overwhelms the atrioventricular node into producing an irregular and rapid heartbeat. As a result, blood pools in the atria that increases a risk for blood clot formation. The major risk factors for atrial fibrillation include age, coronary artery disease, rheumatic heart disease, hypertension, diabetes, and thyrotoxicosis. Atrial fibrillation affects 7% of the population over age 65.

Atrial fibrillation treatment options are limited. Lifestyle change only assists individuals with lifestyle related atrial fibrillation. Medication therapy assists only in the management of atrial fibrillation symptoms, may present side effects more dangerous than atrial fibrillation, and fail to cure atrial fibrillation. Electrical cardioversion attempts to restore sinus rhythm but has a high recurrence rate. In addition, if there is a blood clot in the atria, cardioversion may cause the clot to leave the heart and travel to the brain or to some other part of the body, which may lead to stroke. What are needed are new methods for treating atrial fibrillation and other conditions involving disorganized electrical conduction.

SUMMARY OF THE INVENTION

The present invention relates generally to catheters for performing targeted tissue ablation in a subject. In particular, the present invention provides devices comprising wire tipped and umbrella tipped ablation catheters, and methods for treating conditions (e.g., cardiac arrhythmias) with these devices.

In some embodiments, the present invention provides a device (e.g., for performing at least one function at an internal site in a subject), comprising an elongate catheter body. The elongate catheter body may comprise a proximal end, a distal end, and a spiral tip, wherein the spiral tip is configured for tissue ablation. In addition, the spiral tip may be mounted at the distal end of the elongate catheter body. The spiral tip may be capable of expansion and contraction. In further embodiments, the spiral tip may be mounted either centrally or peripherally with the elongate catheter body. In preferred spiral top embodiments, the spiral tip will be configured to create spiral lesions in targeted body tissue.

In other embodiments, the device may comprise conductive coils on the spiral tip. In particular embodiments, the conductive coils may comprise at least one conductive coil measuring 2-20 millimeters in size. Alternatively, in some embodiments the device may comprise conductive plates on the spiral tip. In particular embodiments, at least one such conductive plate may measure 2-20 millimeters in size.

Embodiments with a spiral tip may have the spiral tip positioned perpendicularly to the distal end of the elongate catheter body. In addition, in some embodiments, the spiral tip may comprise a plurality of loops. In further embodiments the spiral tip may have at least one complete loop. In other embodiments, the spiral tip loops may be separated by gaps. In particular embodiments, such gaps may measure less than 10 millimeters.

Some embodiments may also comprise a handle attached to the proximal end of the elongate catheter body. In further embodiments, the handle may be configured to control expansion or contraction of the spiral tip as well as flexion and extension of the catheter tip. In yet other embodiments, the device will further comprise an energy source configured to permit emission of energy from the spiral tip.

In some embodiments, the present invention provides an elongate catheter body, wherein the elongate catheter body comprises a proximal and distal ends, and an umbrella tip body. In some embodiments, the umbrella tip body may comprise a central post, and a plurality outer arms. In preferred embodiments, the umbrella tip body is configured for tissue ablation. In other embodiments, the umbrella tip body may be mounted at the distal end of the elongate catheter body.

In some embodiments, the present invention provides a central post extending from distal end of said elongate catheter body. In other embodiments, the plurality of outer arms may attach at distal and proximal ends of the central post.

In other embodiments, the device may comprise conductive coils on the outer arms. In particular embodiments, the conductive coils may comprise at least one conductive coil measuring 2-20 millimeters in size. In other embodiments, the conductive coils may comprise at least one conductive coil measuring 4-8 millimeters in size. Alternatively, in some embodiments the device may comprise conductive plates on the outer arms. In particular embodiments, at least one such conductive plate may measure 2-20 millimeters in size. In other embodiments, the conductive plates may comprise at least one conductive plate measuring 4-8 millimeters in size. In preferred embodiments, the umbrella tip may be configured to create radial lesions in body tissue.

Some embodiments may also comprise a handle attached to the proximal end of the elongate catheter body. In further embodiments, the handle may be configured to control expansion or contraction of the umbrella tip body as well as flexion and extension of the catheter tip. In yet other embodiments, the device will further comprise an energy source configured to permit emission of energy from the umbrella tip body.

In some embodiments, the present invention provides a method of treating body tissues. In such embodiments, the method comprises the steps of providing a device, and detailed treatment steps. In other embodiments, the present invention provides a radio-frequency energy source.

In particular embodiments, the device may comprise an elongate catheter body, wherein the elongate catheter body comprises a proximal end and a distal end, and also a spiral tip, wherein the spiral tip may be configured for tissue ablation, the spiral tip mounted at the distal end of the elongate catheter body, and is capable of expansion and contraction.

In other particular embodiments, the device may comprise an elongate catheter body, wherein the elongate catheter body comprises a proximal end and a distal end, and also an umbrella tip body, wherein the umbrella tip body may be configured for tissue ablation, the umbrella tip body is mounted at the distal end of the elongate catheter body, and the umbrella tip body is capable of expansion and contraction. In still further embodiments, the umbrella tip may comprise a central post, and a plurality of outer arms.

In some embodiments, the detailed treatment steps may comprise the inserting of the catheter through a major vein or artery, the guiding of the catheter to the selected body tissue site by appropriate manipulation through the vein or artery, the guiding of the catheter to the selected body tissue site, the positioning of the device with the selected body tissue; and the releasing of energy from the device into the body tissue.

In particular embodiments, the detailed treatment steps may be specific for treating atrial fibrillation, and comprise the inserting of the catheter through a major vein or artery, the guiding of the catheter into the atria of the heart by appropriate manipulation through the vein or artery, the guiding of the catheter to the target atrial region, the positioning the device with the targeted atrial region; and a releasing of energy from the device into the targeted atrial region.

In still further embodiments, the detailed treatment steps may be specific for treating cardiac arrhythmias, and comprise the inserting of the catheter through a major vein or artery, the guiding of the catheter into the heart by appropriate manipulation through the vein or artery, the guiding of the catheter to the targeted heart region, the positioning of the device with the targeted heart region; and the releasing of energy from the device into the targeted heart region.

GENERAL DESCRIPTION OF THE INVENTION

Figure 1:
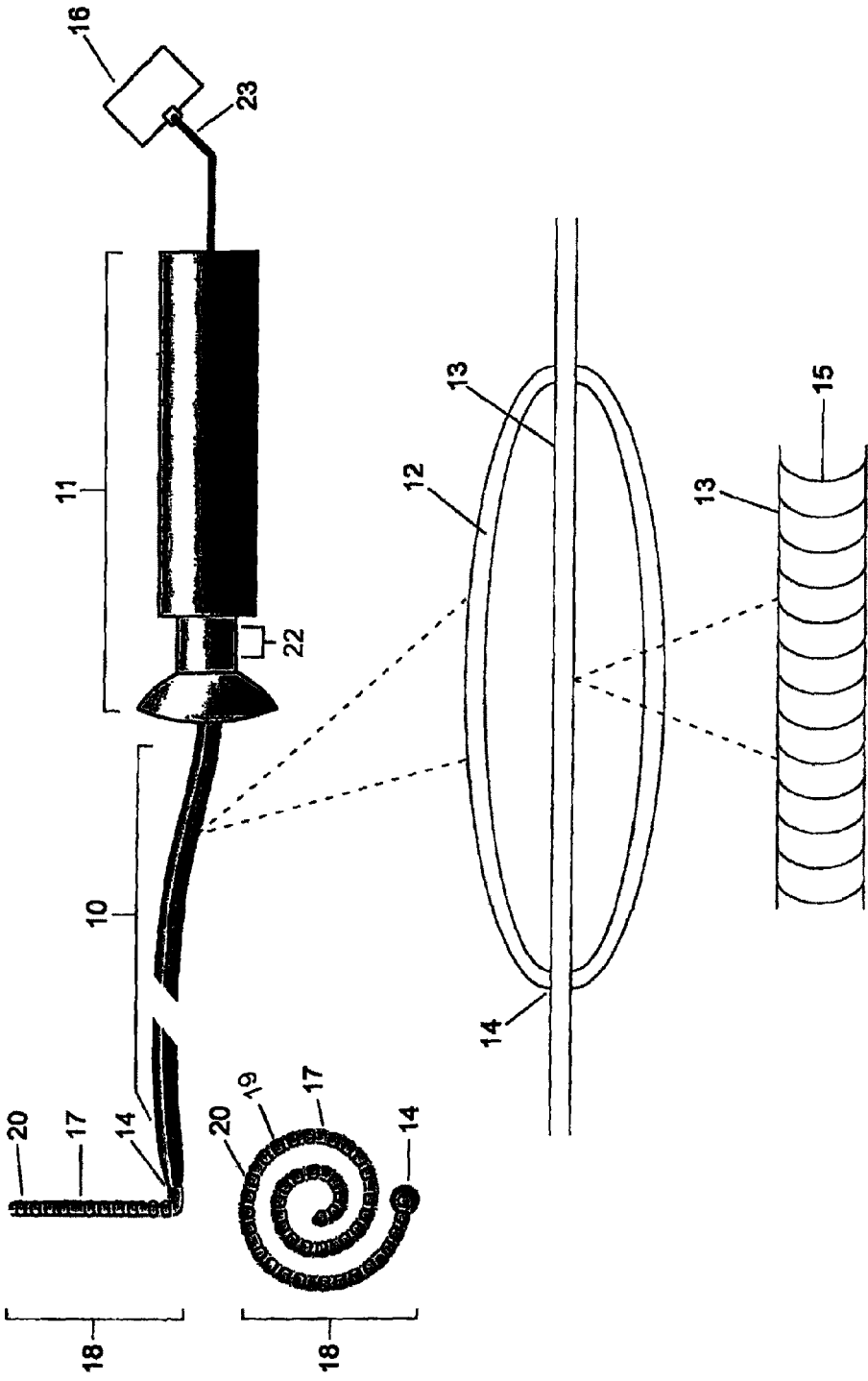
FIG. 1 shows one wire tip ablation catheter embodiment.

The present invention provides catheters for performing targeted tissue ablation in a subject. In particular, the present invention provides devices comprising wire tipped and umbrella tipped catheter ablation devices, and methods for treating conditions (e.g., super ventricular tachycardia with these devices.

As described above, the normal functioning of the heart relies on proper electrical impulse generation and transmission. In certain heart diseases (e.g., atrial fibrillation) proper electrical generation and transmission are disrupted. In order to restore proper electrical impulse generation and transmission, the catheters of the present invention may be employed.

In general, catheter ablation therapy provides a method of treating cardiac arrhythmias. Physicians make use of catheters to gain access into interior regions of the body. Catheters with attached ablating devices are used to destroy targeted tissue. In the treatment of cardiac arrhythmias, a specific area of cardiac tissue emitting or conducting erratic electrical impulses is initially localized. A user (e.g., a physician) will direct a catheter through a main vein or artery into the interior region of the heart that is to be treated. The ablating element is next placed near the targeted cardiac tissue that is to be ablated. The physician directs an energy source from the ablating element to ablate the tissue and form a lesion. In general, the goal of catheter ablation therapy is to destroy cardiac tissue suspected of emitting erratic electric impulses, thereby curing the heart of the disorder. For treatment of atrial fibrillation currently available methods have shown only limited success and/or employ devices that are not practical.

The ablation catheters of the present invention allow the generation of lesions of appropriate size and shape to treat conditions involving disorganized electrical conduction (e.g., atrial fibrillation). The ablation catheters of the present invention are also practical in terms of ease-of-use and risk to the patient. In general, no catheter technique has been shown to have a high efficacy in treatment of persistent atrial fibrillation. Catheters that generate linear or curvilinear lesions in the left or right atrial tissue have a very limited efficacy. Moreover, the procedure length and the incidence of complications are significantly high with current approaches. Another approach utilizes encircling of the left atrial tissue by point-by-point applications. An additional approach utilizes encircling of the left atrial tissue by point-by-point applications of radio-frequency energy. However, to generate complete circles this approach is time consuming and has limited efficacy. The present invention addresses this need with, for example, wire tip and umbrella ablation catheters and methods of using these ablation catheters to create spiral or radial lesions in the endocardial surface of the atria by delivery of energy (e.g., radio-frequency). The lesions created by the wire tipped and umbrella tipped ablation catheters are suitable for inhibiting the propagation of inappropriate electrical impulses in the heart for prevention of reentrant arrhythmias.

Definitions

To facilitate an understanding of the invention, a number of terms are defined below.

As used herein, the terms "subject" and "patient" refer to any animal, such as a mammal like livestock, pets, and preferably a human. Specific examples of "subjects" and "patients" include, but are not limited, to individuals requiring medical assistance, and in particular, requiring atrial fibrillation catheter ablation treatment.

As used herein, the terms "catheter ablation" or "ablation procedures" or "ablation therapy," and like terms, refer to what is generally known as tissue destruction procedures. Ablation is often used in treating several medical conditions, including abnormal heart rhythms. It can be performed both surgically and non-surgically. Non-surgical ablation is typically performed in a special lab called the electrophysiology (EP) laboratory. During this non-surgical procedure a catheter is inserted into the heart and then a special machine is used to direct energy to the heart muscle. This energy either "disconnects" or "isolates" the pathway of the abnormal rhythm (depending on the type of ablation). It can also be used to disconnect the electrical pathway between the upper chambers (atria) and the lower chambers (ventricles) of the heart. For individuals requiring heart surgery, ablation can be performed during coronary artery bypass or valve surgery.

As used herein, the term "wire tip body" refers to the distal most portion of a wire tip catheter ablation instrument. A wire tip body is not limited to any particular size. A wire tip body may be configured for energy emission during an ablation procedure.

As used herein, the term "spiral tip" refers to a wire tip body configured into the shape of a spiral. The spiral tip is not limited in the number of spirals it may contain. Examples include, but are not limited to, a wire tip body with one spiral, two spirals, ten spirals, and a half of a spiral.

As used herein the term "umbrella tip body" refers to the distal most portion of an umbrella tip catheter ablation instrument. An umbrella tip body is not limited to any particular size. An umbrella tip body may be configured for energy emission during an ablation procedure.

As used herein, the term "lesion," or "ablation lesion," and like terms, refers to tissue that has received ablation therapy. Examples include, but are not limited to, scars, scabs, dead tissue, and burned tissue.

As used herein, the term "spiral lesion" refers to an ablation lesion delivered through a spiral tip ablation catheter. Examples include, but are not limited to, lesions in the shape of a wide spiral, and a narrow spiral.

As used herein, the term "umbrella lesion" or "radial lesion," and like terms, refers to an ablation lesion delivered through an umbrella tip ablation catheter. Examples include, but are not limited to, lesions with five equilateral prongs extending from center point, lesions with four equilateral prongs extending from center point, lesions with three equilateral prongs extending from a center point, and lesions with five non-equilateral prongs extending from center point.

As used herein, the term "conductive coil" refers to electrodes capable of emitting energy from an energy source in the shape of a coil. A conductive coil is not limited to any particular size or measurement. Examples include, but are not limited to, densely wound copper, densely wound platinum, and loosely wound silver.

As used herein, the term "conductive plate" refers to electrodes capable of emitting energy from an energy source in the shape of a plate. A conductive plate is not limited to any particular size or measurement. Examples include, but are not limited to, copper plates, silver plates, and platinum plates.

As used herein, the term "energy" or "energy source," and like terms, refers to the type of energy utilized in ablation procedures. Examples include, but are not limited to, radio-frequency energy, microwave energy, cryo-energy energy (e.g., liquid nitrogen), or ultrasound energy.

As used herein, the term "maze procedure," "maze technique," "maze ablation," and like terms, refer to what is generally known as a cardiac ablation technique. Small lesions are made at a specific location in the heart in a manner so as to create a "maze." The maze is expected to prevent propagation of electrical impulses.

As used herein, the term "central post" refers to a chamber capable of housing small items. The central post is made from a durable material. A central post is not limited to any particular size or measurement. Examples include, but are not limited to, polyurethane, steel, titanium, and polyethylene.

As used herein, the term "outer arms" refers to a shaft capable of interfacing with electrodes and a central post. An outer arm is not limited to any size or measurement. Examples include, but are not limited, to titanium shafts, polyurethane shafts, and steel shafts.

As used herein, the term "outer arm hinge" refers to a joint (e.g., junction, flexion point) located on an outer arm. The degree of flexion for an outer arm hinge may range from 0 to 360 degrees.

DETAILED DESCRIPTION OF THE INVENTION

The present invention provides structures that embody aspects of the ablation catheter. The present invention also provides tissue ablation systems and methods for using such ablation systems. The illustrated and preferred embodiments discuss these structures and techniques in the context of catheter-based cardiac ablation. These structures, systems, and techniques are well suited for use in the field of cardiac ablation.

However, it should be appreciated that the invention is applicable for use in other tissue ablation applications. For example, the various aspects of the invention have application in procedures for ablating tissue in the prostrate, brain, gall bladder, uterus, and other regions of the body, using systems that are not necessarily catheter-based.

The multifunctional catheters of the present invention have advantages over previous prior art devices. FIGS. 1-11 show various preferred embodiments of the multifunctional catheters of the present invention. The present invention is not limited to these particular configurations.

Wire Tip Ablation Catheters

FIG. 1 illustrates an ablation catheter embodiment including broadly an elongate catheter body 10 (e.g., hollow tube) extending from a handle 11. Elongate catheter body 10 permits the housing of items that assist in the ablation of subject tissue (e.g., human tissue and other animal tissue, such as cows, pigs, cats, dogs, or any other mammal). The elongate catheter body 10 may range in size so long as it is not so small that it cannot carry necessary ablation items, and not so large so that it may not fit in a peripheral major vein or artery. The elongate catheter body 10 includes an elongate sheath 12 (e.g., protective covering). The elongate sheath 12 may be made of a polymeric, electrically nonconductive material, like polyethylene or polyurethane. In preferred embodiments, the elongate sheath 12 is formed with the nylon based plastic Pbax, which is braided for strength and stability. In additional embodiments, the elongate sheath 12 is formed with hypo tubing (e.g., stainless steel, titanium). The elongate sheath 12 houses a conducting wire 13 (e.g., standard electrical wire) and a thermal monitoring circuit 19. The conducting wire extends from the handle 11 through the distal opening 14. In addition, the conducting wire 13 is wrapped with a steering spring 15. The conducting wire 13 is flexible so that it may be flexed to assume various positions (e.g., curvilinear positions). The steering spring 15 is controlled through manipulation of the handle 11, as discussed below. The conducting wire 13 is also capable of transmitting energy (e.g., radio-frequency energy) from an energy source 16 (e.g., radio-frequency energy generator).

A thermal monitoring circuit 19 (e.g., thermocouple) is coupled with the conducting wire 13 and extends from the handle 11 through the umbrella tip body 25. The thermal monitoring circuit 19 connects with energy source cable 23 within handle 11. Regulation of the thermal monitoring circuit 19 is achieved through the energy source 16. In some embodiments, the present invention utilizes the thermal monitoring circuit described in U.S. Pat. No. 6,425,894 (herein incorporated by reference), whereby a thermocouple is comprised of a plurality of thermal monitoring circuits joined in series. The thermal monitoring circuits are thermoconductively coupled to the electrodes. In some embodiments, the thermal monitoring circuit employs two wires to travel through the elongated catheter body in order to monitor a plurality of electrodes.

The distal opening 14 is the distal terminus of the elongate catheter body 10. At the distal opening 14, the conducting wire 13 exits the elongate sheath 12. While the majority of the conducting wire 13 is housed within the elongate sheath 12, the distal portion is housed within the wire tip sheath 17. The wire tip sheath 17 begins at the distal opening 14 and extends throughout the wire tip body 18. The wire tip sheath 17 may be made of a polymeric, electrically nonconductive material (e.g., polyethylene or polyurethane). In preferred embodiments, the wire tip sheath 17 is formed with peek insulator (e.g., high temperature thermo-plastic). A thermal monitoring circuit 19 is coupled with the conducting wire 13 and extends from the handle 11 through the wire tip body 18. The thermal monitoring circuit 19 connects with energy source cable 23 within handle 11.

The wire tip sheath 17 permits the wire tip body 18 to be molded or shaped into a desired position. In preferred embodiments, the wire tip body 18 may be shaped into a unique shape (e.g., spiral).

Figure 2:
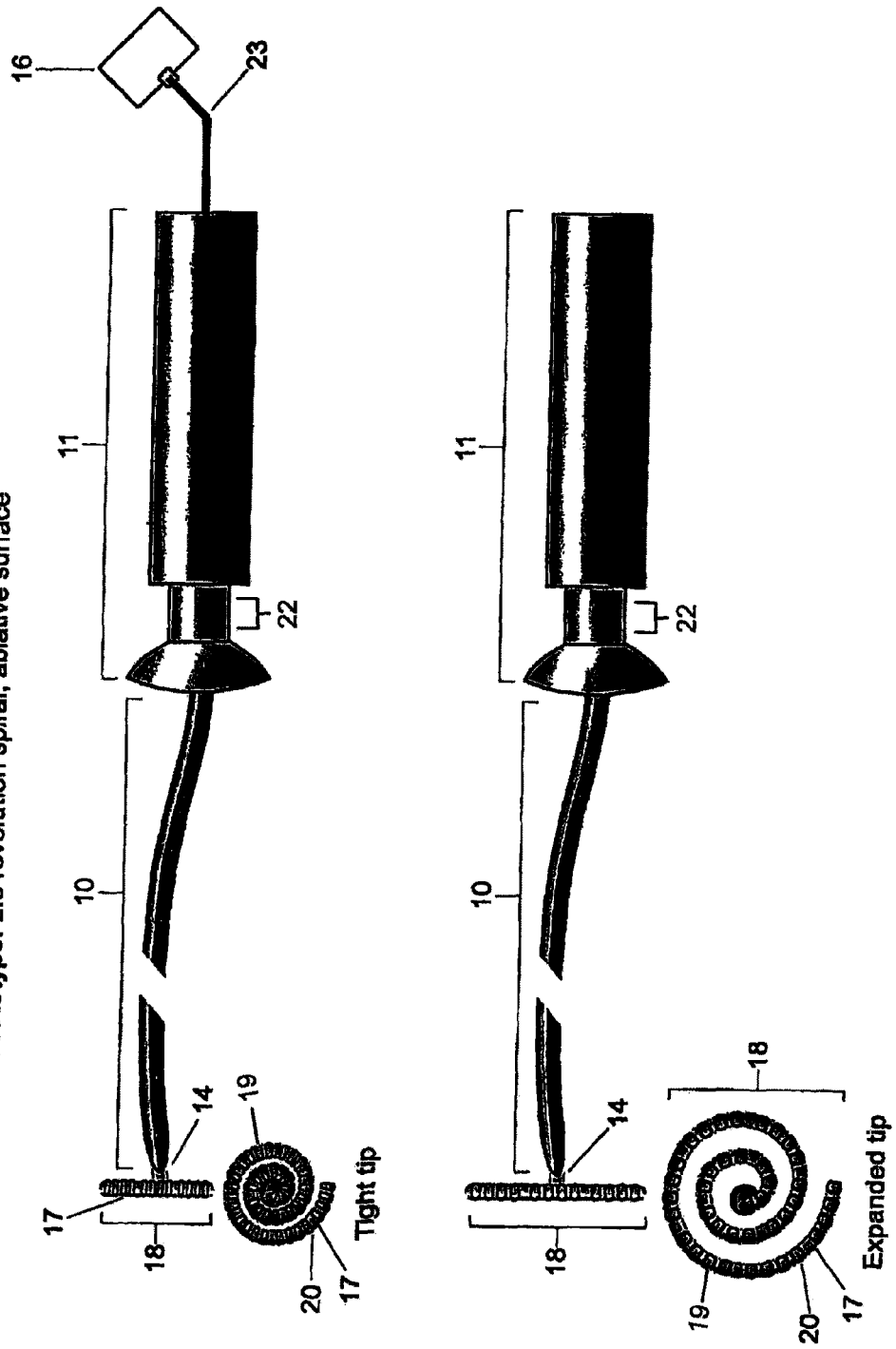
FIG. 2 shows one embodiment of the wire tip ablation catheter.
Figure 3:
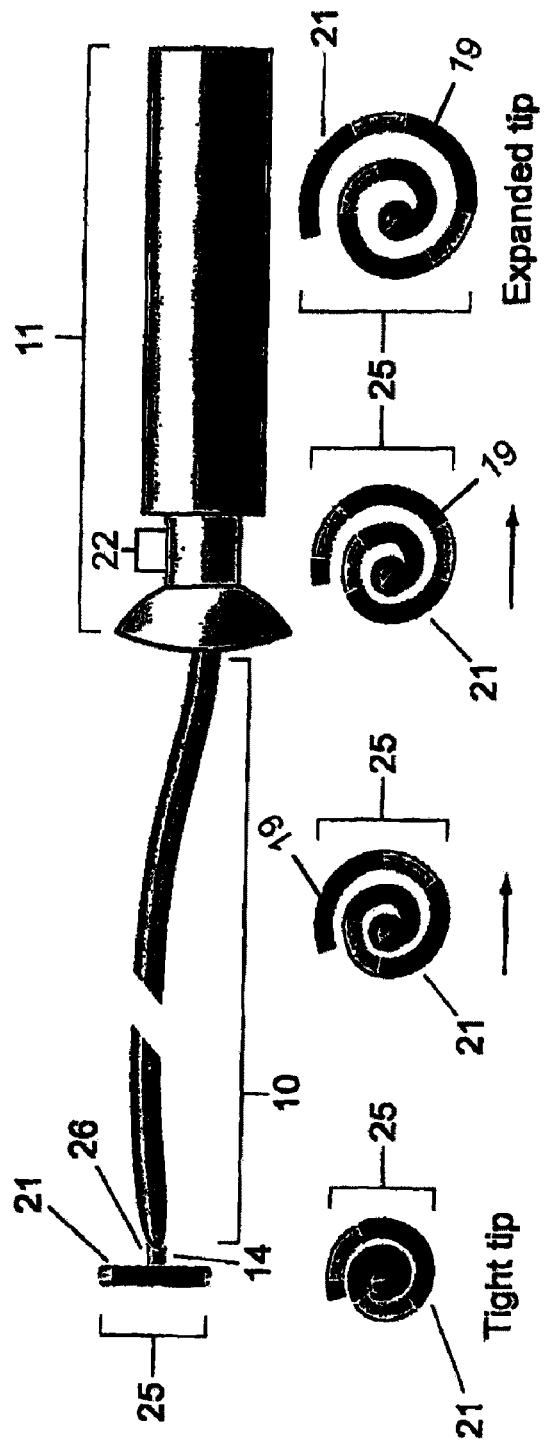
FIG. 3 shows one embodiment of the wire tip ablation catheter utilizing conductive plates.

In the preferred embodiment described FIGS. 1-4, the wire tip body 18 is in the shape of a spiral. The spiral on a wire tip body 18 may be peripheral to or central to the elongate catheter body 10. The spiral wire tip body 18 is central if the spiral interfaces with the distal opening 14 at the spiral center point, and peripheral if the spiral interfaces with the distal opening 14 at the spiral exterior point. The embodiment described in FIG. 1 presents a spiral wire tip body 18 that is peripheral to the elongate catheter body 10. Alternatively, the embodiment described in FIG. 2 presents a spiral wire tip body 18 that is central to the elongate catheter body. A wire tip body 18 in the shape of a spiral may comprise any number of complete rotations (e.g., complete spirals). In the embodiment described in FIGS. 1 and 2, the spiral wire tip body 18 consists of two and one half complete rotations. Alternatively, the embodiment described in FIG. 3 presents a spiral with only two complete rotations. The distance inbetween the spirals on the wire tip body 18 may assume any measurement.

Tissue ablation occurs on the wire tip body 18. Various conductive elements (e.g., coils or plates) may be distributed along the wire tip body 18. The energy utilized within a catheter ablation instrument is released through the conductive elements. The number of conductive elements on the wire tip body 18 permit a determined energy release and resulting ablation lesion.

Figure 4:
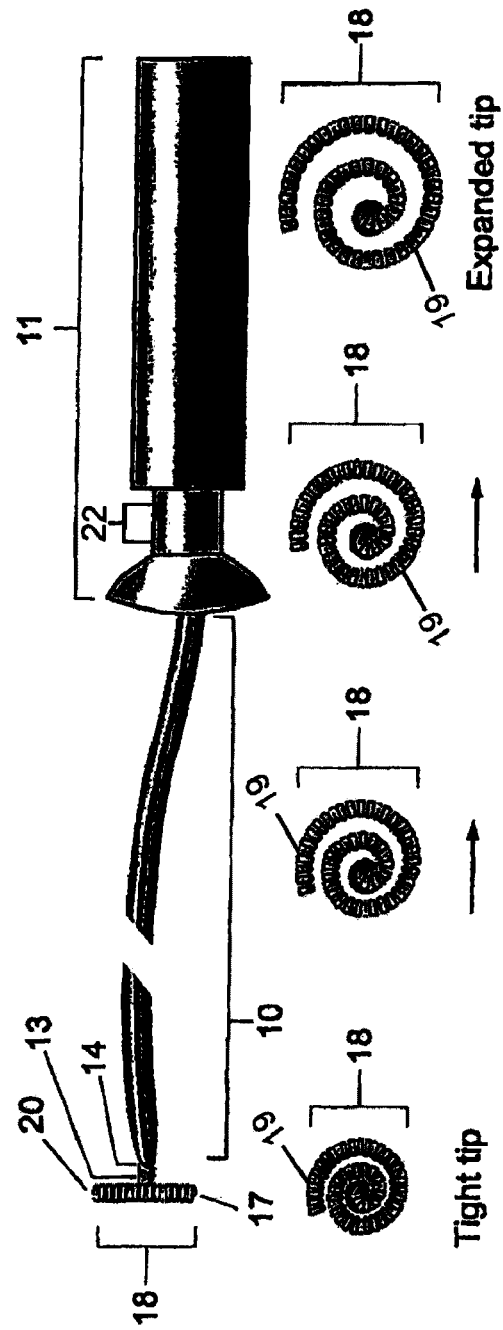
FIG. 4 shows one embodiment of the wire tip ablation catheter utilizing conductive coils.
Figure 5:
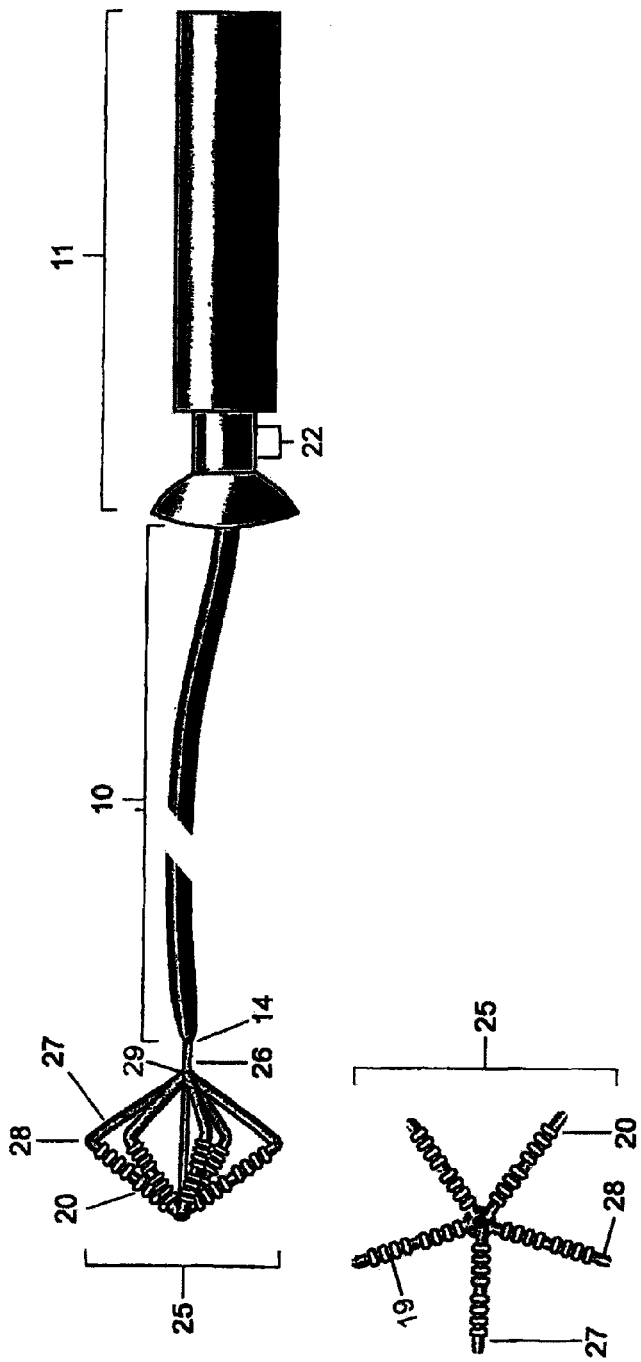
FIG. 5 shows one embodiment of the umbrella tip ablation catheter.
Figure 6:
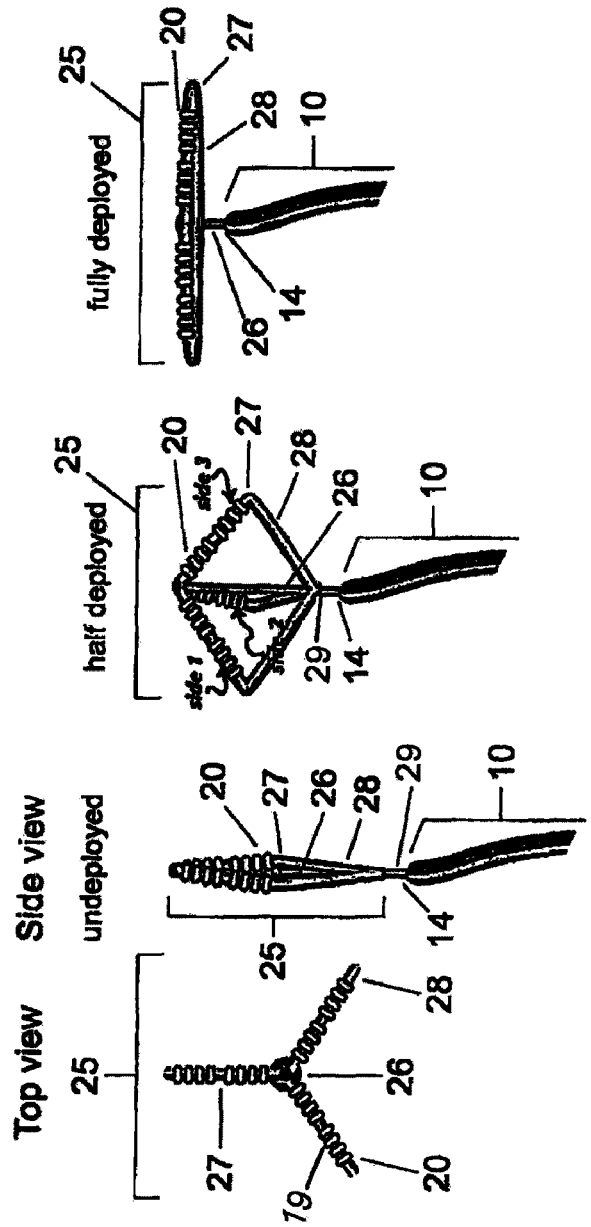
FIG. 6 shows one embodiment of the umbrella tip ablation catheter.

The conductive elements used in the preferred embodiment described in FIGS. 1, 2 and 4 are conductive coils 20. Each conductive coil 20 is an electrode that is comprised of a densely wound continuous ring of conductive material, (e.g., silver, copper). In preferred embodiments, the conductive coil 20 is made from platinum. The conductive coils 20 are fitted (e.g., pressure fitting) about the wire tip body 18. In preferred embodiments, a conductive coil 20 is soldered onto a conductive metal (e.g., copper, copper with silver) and swaged onto the wire tip body 18. Additional embodiments may utilize an adhesive seal in addition to swaging in fixing conductive coils 20 to the wire tip body 18. A conductive coil 20 may range in size from 0.1 mm to 20 mm. In preferred embodiments, a conductive coil 20 ranges in size from 2 to 8 mm. The conductive coils 20 interact with the conducting wire 13 and emit the energy carried by the conductive wire 13.

Conductive coils 20 may be arranged in many different patterns (e.g., staggered) along the wire tip body 18. Such patterns may involve repeating sets of conductive coils 20 (e.g., set of 3 coils-3 coils-3 coils, etc.) or nonrepeating sets (e.g., set of 3 coils-5 coils-2 coils, etc.). In addition, the pattern of conductive coils 20 may simply involve only one coil instead of sets. The pattern of conductive coils 20 arranged in the preferred embodiment presented in FIGS. 1, 2 and 4 consist of a repeating set of four conductive coils 20 separated by a gap. In general, the gap may range in size from 0.1 mm to 100 mm, and is nonconductive. In the embodiments demonstrated in FIGS. 1, 2 and 4, the gap size is 5 mm. Within a repeating arrangement of conductive coils 20, the spaces in between the conductive coils 20 are also nonconductive and may range in size from 0.01 mm to 100 mm.

The conductive elements used in the preferred embodiment described in FIG. 3 are conductive plates 21. Each conductive plate 21 is an electrode that is comprised of a solid ring of conductive material (e.g., platinum). The conductive plates 21 are fitted (e.g., pressure fitting) about the wire tip body 18. Additional embodiments may utilize an adhesive seal in addition to swaging in fixing conductive plates 21 to the wire tip body 18. A conductive plate 21 may range in size from 0.1 mm to 20 mm. The conductive plates 21 interact with the conducting wire 13 and emit the energy carried by the conductive wire 13.

Conductive plates 21 may be arranged in many different patterns (e.g., repeating sets) along the wire tip body 18. Such patterns may involve a repeating series of conductive plates 21 separated by spaces (e.g., plate-space-plate-space-plate; etc.) or a random series (e.g., space-space-plate-plate-plate-space-plate; etc.). In addition, the pattern of conductive plates 21 may simply involve only one short or extended conductive plate 19. The pattern arranged in the preferred embodiment presented in FIG. 3 consists of four conductive plates 21 separated by nonconductive gaps. In general, the gaps may range in size from 0.1 mm to 100 mm. In the FIG. 4 embodiment, the gap size is 5 mm.

The pattern of conductive elements arranged on the wire tip body 18 need not be restricted to only a certain type. Indeed, the present invention envisions a wire tip body 18 with varied patterns of different conductive elements (e.g., coil-gap-plate-plate-gap-coil-coil; etc.).

The wire tip body 18 may be expanded or contracted through manipulation of the handle 11. In preferred embodiments, the handle 11 connects with the conducting wire 13 with the steering spring 15 attached onto it. The conducting wire 13 attaches onto a lever 22 inside the handle 11. Extension of the lever 22 causes a contraction in the steering spring 15 attached to the conducting wire 13 resulting in a constricting of the wire tip body 18. Alternatively, constriction of the lever 22 causes the steering spring 15 to expand.

An alternative embodiment utilizes the steering method described in U.S. Pat. No. 5,318,525 (herein incorporated by reference). In that embodiment, a catheter tip is deflected by means of a shapable handle coupled to pull wires fastened to the distal end of the deflectable tip. A core wire extends from the handle to the distal tip, providing fine positioning of the deflectable tip by applying torque through the core wire to the tip. A spring tube is further provided in the deflectable tip for improved torque transmission and kink-resistance. The catheter has an electrode at the distal end of the deflectable tip for positioning at a target site and applying RF power to accomplish ablation.

In other embodiments, the method of catheter manipulation described in U.S. 2001/0044625 A1 (herein incorporated by reference) is utilized, whereby a control element within the handle is able to flex and deflex the distal tip. Additional embodiments utilize the method of catheter manipulation described in U.S. Pat. No. 6,241,728 (herein incorporated by reference), whereby three handle manipulators permit a distal tip to be deflected longitudinally, radially, and in a torqued position. A further embodiment utilizes the method of catheter manipulation described in U.S. 2001/0029366 A1 (herein incorporated by reference), whereby a rotating cam wheel permits the steering of a distal tip in any direction. However, other mechanisms for steering or deflecting the distal end of a catheter according to the present invention may also be employed. For example, the steering and deflection mechanism as set forth in U.S. Pat. No. 5,487,757 may also be employed to deflect the distal tip of the catheter, as well as any other known deflection/steering mechanism. Similarly, a sliding core wire for adjustment of the radius of curvature of the catheter when deflected may also be employed, as also disclosed in U.S. Pat. No. 5,487,757.

In alternative embodiments, the wire tip body 18 may be expanded or contracted though computer assisted manipulation. In other embodiments, the wire tip body 18 may be manipulated through use of magnetic fields.

The terminus of the conducting wire attaches to an energy source cable 23 that establishes a connection with the energy source 16.

Depictions of various degrees of contraction or expansion of the wire tip body 18 in the shape of a spiral are presented in FIGS. 2, 3 and 4. In the fully contracted position, the regions between the spirals on the wire tip body 18 decreases while the spacing in between the conductive elements remains intact. As the wire tip body 18 becomes more expanded, the regions in between spirals on the wire tip body 18 increases, and the spacing in between the conductive elements remains intact.

The proximal origin of the conducting wire 13 may be located at the distal end of the handle 11. At the proximal origin of the conducting wire 13, the conducting wire 13 is connected with an energy source 16 (e.g., radio-frequency energy). Embodiments of the present invention may utilize numerous forms of energy (e.g., radio-frequency energy, liquid nitrogen, saline). In one embodiment, liquid nitrogen is utilized as an energy source 16 (such embodiments employ a hollow tube that travels throughout the catheter to deliver $N_2$ gas) that freezes a particular tissue region. In an additional embodiment, the energy source 16 utilized is a saline irrigation system, whereby saline is flushed out through a mesh of electrodes carrying an electric current.

In preferred embodiments, radio-frequency energy is utilized as the energy source 16. Various radio-frequency energy generators are commercially available. A large (20×10 cm) ground patch is attached to the patient's back to complete the circuit. The current travels from the tip of the heart to the patch. The amount of energy utilized may be controlled by adjusting the power output of the energy source 16. Four parameters may are regulated through the energy source 16: power output, impedance, temperature, and duration of energy application.

The precise pattern of conductive elements assorted on the wire tip body 18 along with the shaped configuration of the wire tip body 18 permits a unique type of ablation lesion ranging from long and thin to large and deep in shape. In addition, numerous types of ablation lesions are possible for each catheter ablator embodiment through manipulation o the wire tip body 18.

Umbrella Tip Ablation Catheters

FIGS. 5-11 illustrate ablation catheter embodiments including broadly an elongate catheter body 10 (e.g., hollow tube) extending from a handle 11. The elongate catheter body 10 includes an elongate sheath 12 (e.g., protective covering). The elongate sheath 12 houses a conducting wire 13 (e.g., standard electrical wire) and a thermal monitoring circuit 19. The conducting wire extends from the handle 11 through the distal opening 14. The conducting wire 13 is also capable of transmitting energy (e.g., radio-frequency energy) from an energy source 16 (e.g., radio-frequency energy generator).

A thermal monitoring circuit 19 (e.g., thermocouple) may be coupled with the conducting wire 13 and extend from the handle 11 through the umbrella tip body 25. The thermal monitoring circuit 19 is connects with energy source cable 23 within handle 11. Regulation of the thermal monitoring circuit 19 is achieved through the energy source 16. In some embodiments, the present invention utilizes the thermal monitoring circuit described in U.S. Pat. No. 6,425,894 (herein incorporated by reference), whereby a thermocouple is comprised of a plurality of thermal monitoring circuits joined in series. The thermal monitoring circuits thermoconductively coupled to the electrodes. The thermal monitoring circuit will require only two wires to travel through the elongated catheter body in order to monitor a plurality of electrodes.

The distal opening 14 is the distal terminus of the elongate catheter body 10. The most distal portion of this embodiment is the umbrella tip body 25. The umbrella tip body 25 consists of a central post 26, a plurality of outer arms 27, the conductive wire 13, and conductive elements (e.g., coils).

The central post 26 extends from the distal opening 14. The central post 26 is a chamber (e.g., hollow tube) capable of housing small items (e.g., wire). The central post 26 may be made from electrically nonconductive materials (e.g., polyurethane, plastic, or polyethylene). The length of the central post 26 may range from 0.1 mm to 100 mm, and its diameter from 0.001 mm to 100 mm. The central post 26 may be formed into numerous shapes. In the preferred embodiments described in FIGS. 5-11, the central post 26 is in the shape of an extended cylindrical rod.

One function of the central post 26 is to house the conducting wire 13. At the distal opening 14, the conducting wire 13 exits the elongate sheath 12. While the majority of the conducting wire 13 is housed within the elongate sheath 12, the distal portion is housed within the central post 26.

The outer arms 27 extend from the base of the central post 26 through the top of the central post 26. An outer arm 27 is a shaft (e.g., post) made from an electrically nonconductive material (e.g., polyurethane, polyethylene). The length of an outer arm 27 may range from 0.1 mm to 100 mm, and its diameter from 0.001 mm to 100 mm. In some embodiments, along the outside of an outer arm 27 is a thermal monitoring circuit 19, which is able to detect temperature and maintain temperature.

An outer arm 27 may be flexible or rigid. In the preferred embodiments described in FIGS. 5-11, the outer arms 27 are flexible. The degree of flexibility may range from 0 to 360 degrees. There are several types of outer arm 27 flexibility. The outer arm 27 flexibility displayed in FIGS. 5-11 arises from an outer arm hinge 28 located at the outer arm's 27 midpoint and permits a degree of flexibility from 0 to 180 degrees.

One function of the outer arms 27 is to interact with the central post 26. The central post 26 and each outer arm 27 firmly connect (e.g., adhere) at the top of the central post 26. The outer arms 27 also interface (e.g., connect) at the base of the central post 26. The outer arm 27 connections at the base of the central post 26 may or may not also connect with the central post 27. In the preferred embodiments described in FIGS. 5-11, the outer arms 27 interface together at the distal opening 14 at a distal opening ring 29. The distal opening ring 29 does not connect to the central post 26, but rather connects to the distal opening 14.

Umbrella tip bodies 25 may present a plurality of outer arms 27. The embodiments described in FIGS. 5, 10 and 11 display an umbrella tip 26 with five outer arms 27. The embodiments described in FIGS. 6 and 7 display an umbrella tip body 26 with three outer arms 27. The embodiments described in FIGS. 8 and 9 display an umbrella tip body 26 with four outer arms 27. There may be any range of distances in between each outer arm 27 on an umbrella tip 26. In the embodiments displayed in FIGS. 5-11 the distances in between each outer arm 27 are equilateral.

Conductive elements (e.g., plates) are distributed along the outer arms 27. The energy utilized within a catheter ablation instrument is released through the conductive elements. The number of conductive elements an outer arm 27 permits a determined energy release and resulting ablation lesion.

The conductive elements used in the preferred embodiments described in FIGS. 5, 6, 8, and 10 are conductive coils 20. Each conductive coil 20 is an electrode that is comprised of a densely wound continuous ring of conductive material, (e.g., silver, copper). In preferred embodiments, the conductive coil 20 is made from platinum. The conductive coils 20 are fitted (e.g., pressure fitting) about the wire tip body 18. In preferred embodiments, a conductive coil 20 is soldered onto a conductive metal (e.g., copper, copper with silver) and swaged onto the umbrella tip body 25. Additional embodiments may utilize an adhesive seal in addition to swaging in fixing conductive coils 20 to the umbrella tip body 25. A conductive coil 20 may range in size from 0.1 mm to 20 mm. The conductive coils 20 interact with the conducting wire 13 and emit the energy carried by the conducting wire 13.

Conductive coils 20 may be arranged in many different patterns (e.g., staggered) along an outer arm 27. Such patterns may involve repeating sets of conductive coils 20 (e.g., set of 3 coils-3 coils-3 coils, etc.) or nonrepeating sets (e.g., set of 3 coils-5 coils-2 coils, etc.). The pattern of conductive coils 20 may simply involve only one coil instead of sets. In addition, an umbrella tip body 26 may vary the patterns of conductive coils 20 on each outer arm 27 to achieve an even more unique ablation lesion. The pattern of conductive coils 20 arranged in the preferred embodiment presented in FIGS. 5, 6, 8, and 10 consist of two sets of four conductive coils 20 separated by a gap on each outer arm 27 located near the distal ending. In general, the gaps may range in size from 0.1 mm to 100 mm, and is nonconductive. Within a repeating arrangement of conductive coils 20, the spaces in between the conductive coils 20 are also nonconductive and may range in size from 0.01 mm to 100 mm.

Figure 7:
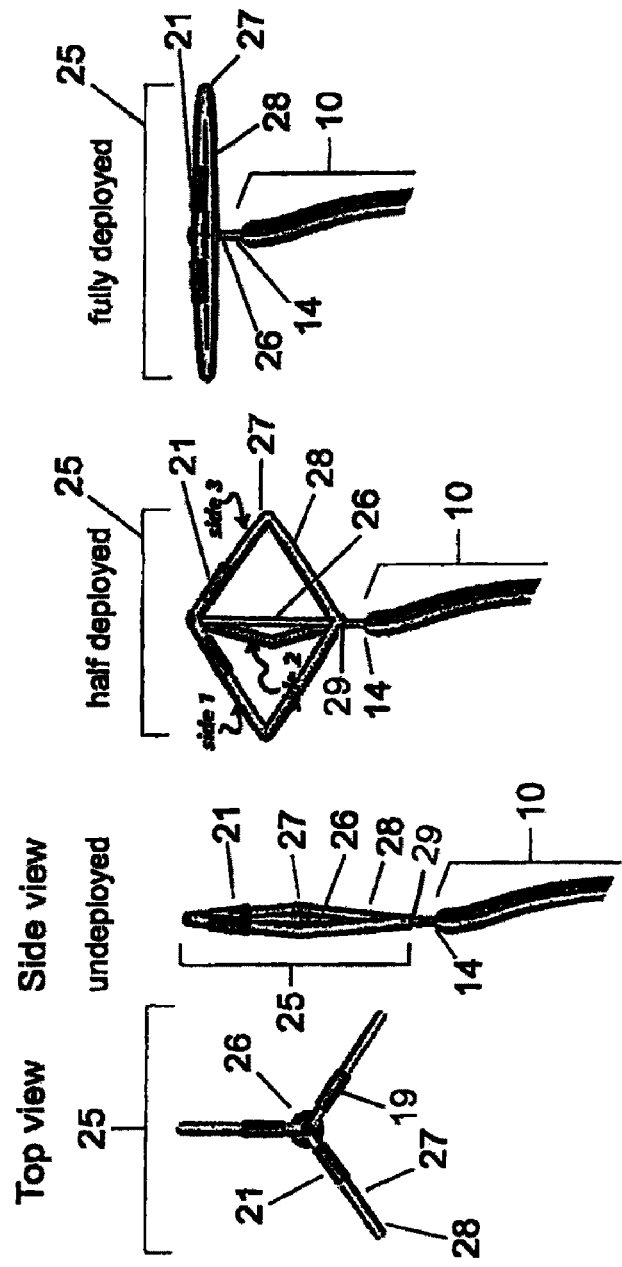
FIG. 7 shows one embodiment of the umbrella tip ablation catheter.
Figure 8:
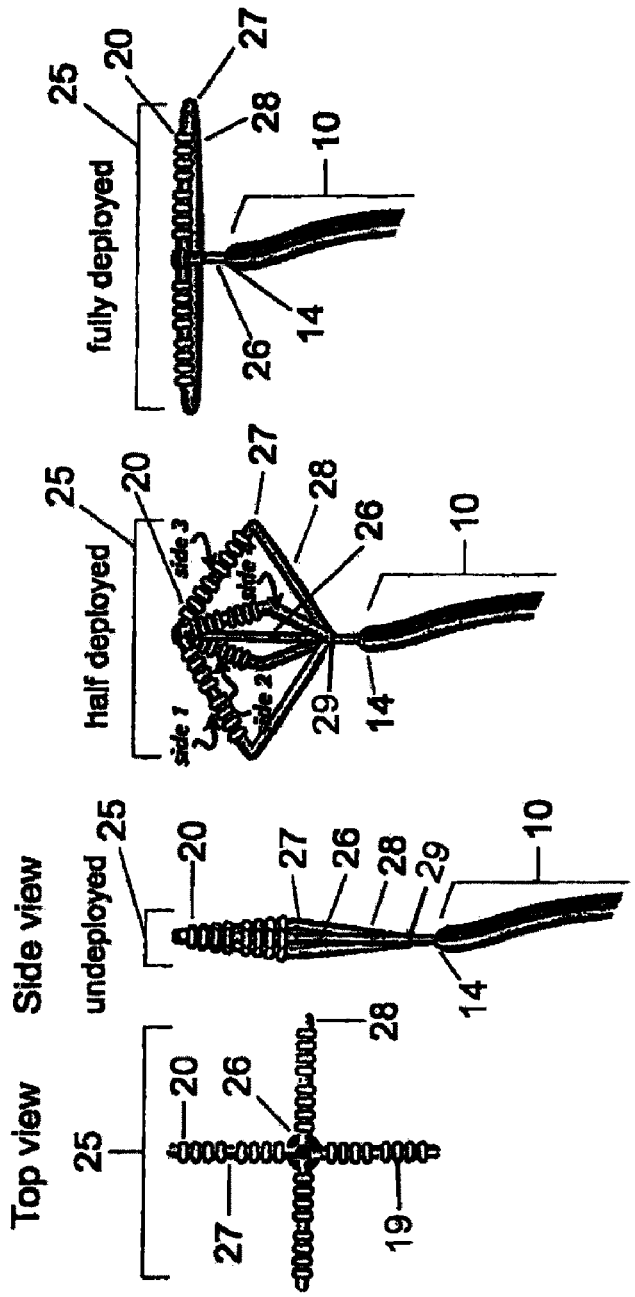
FIG. 8 shows one embodiment of the umbrella tip ablation catheter.
Figure 9:
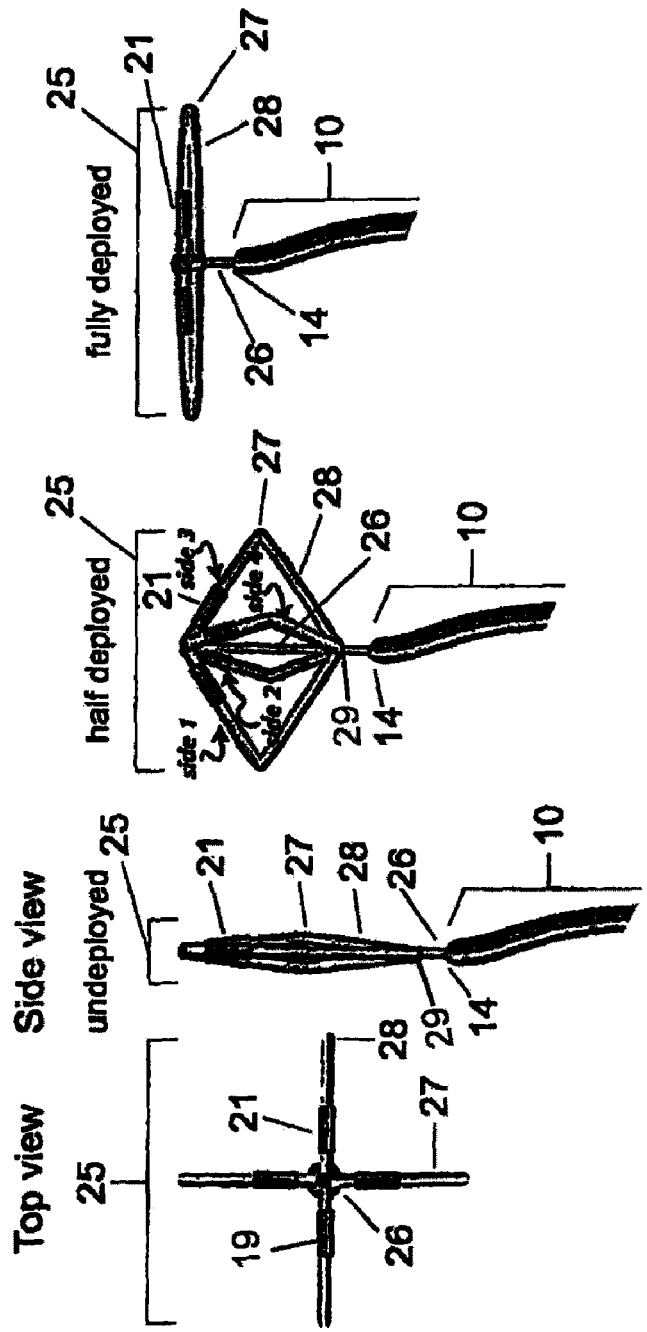
FIG. 9 shows one embodiment of the umbrella tip ablation catheter.
Figure 10:
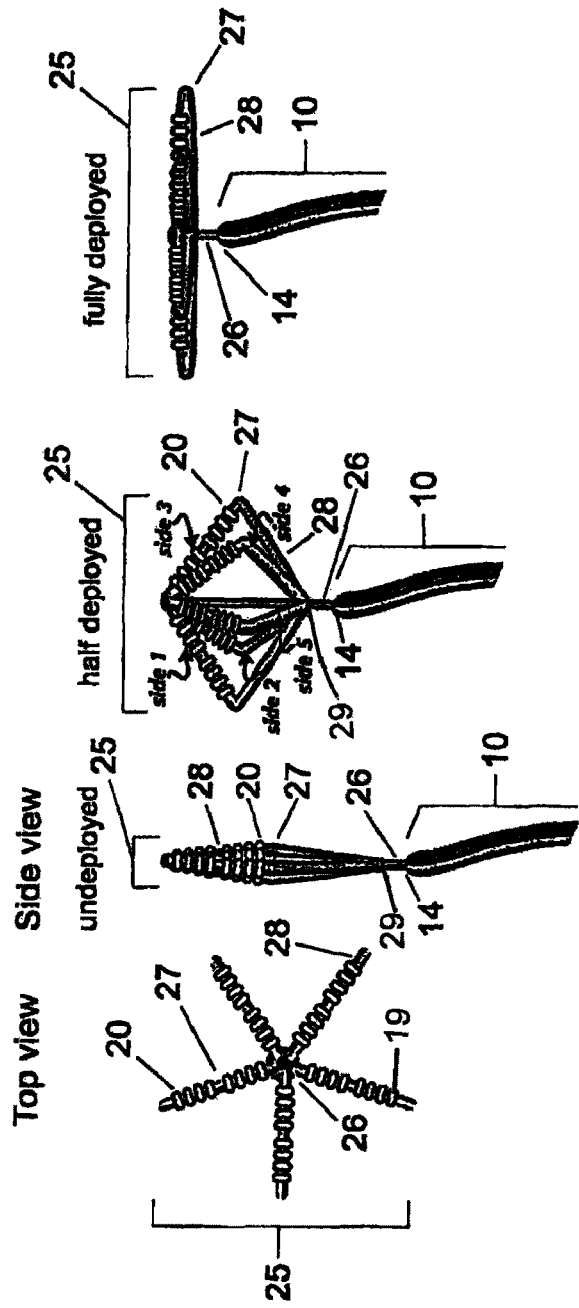
FIG. 10 shows one embodiment of the umbrella tip ablation catheter.
Figure 11:
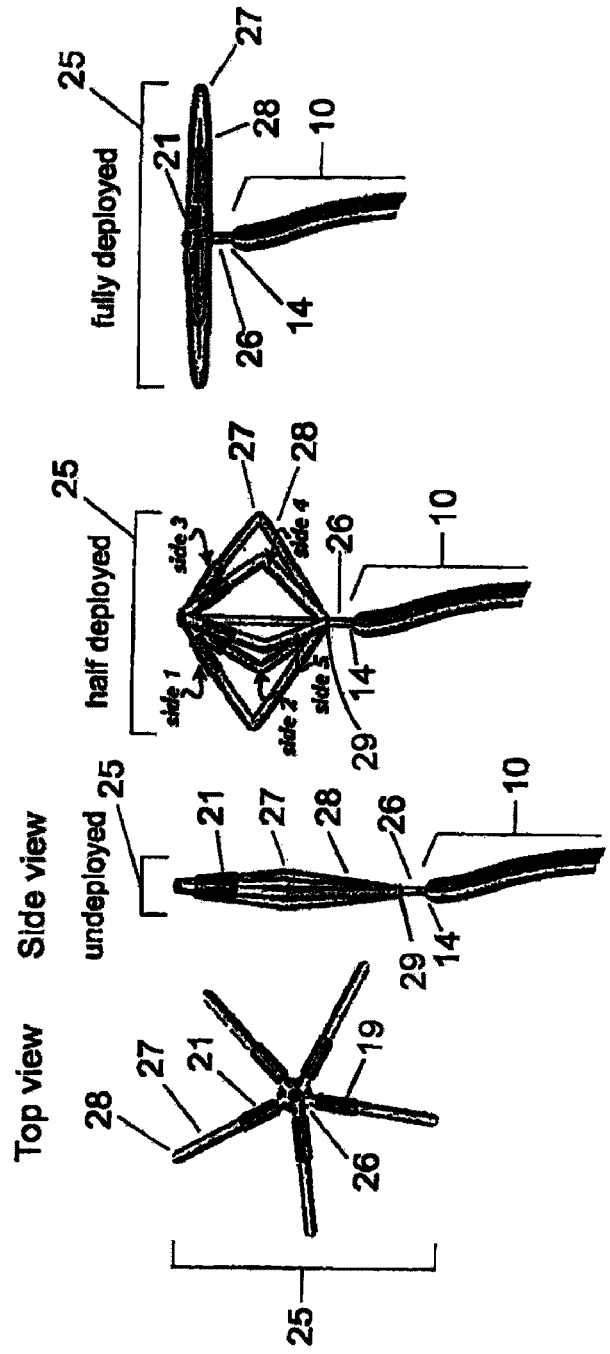
FIG. 11 shows one embodiment of the umbrella tip ablation catheter.

The conductive elements used in the preferred embodiment described in FIGS. 7, 9, and 11 are conductive plates 21. Each conductive plate 21 is an electrode that is comprised of a solid ring of conductive material, (e.g., platinum). The conductive plates 21 are fitted (e.g., pressure fitting) about an outer arm 27. A conductive plate 21 may range in size from 0.1 mm to 20 mm. The conductive plates 19 interact with the conducting wire 13 and emit the energy carried by the conducting wire 13.

Conductive plates 21 may be arranged in many different patterns (e.g., repeating sets) along an outer arm 27. Such patterns may involve a repeating series of conductive plates 21 separated by spaces (e.g., plate-space-plate-space-plate; etc.) or a random series (e.g., space-space-plate-plate-plate-space-plate; etc.). The pattern of conductive plates 21 may simply involve only one short or extended conductive plate 21. In addition, an umbrella tip body 26 may vary the patterns of conductive plates 21 on each outer arm 27 to achieve an even more unique ablation lesion. The pattern arranged in the preferred embodiment presented in FIGS. 7, 9, and 11 consists of one conductive plates 21 on each outer arm 27 located near the distal ending.

The pattern of conductive elements arranged on the umbrella tip body 26 need not be restricted to only a certain type. Indeed, the present invention contemplates an umbrella tip 26 with varied patterns of different conductive elements (e.g., outer arm 1: coil-plate-plate-coil; outer arm 2: plate-plate-coil; outer arm 3: coil-coil; etc.).

An umbrella tip 26 may be expanded or contracted through manipulation of the handle 11. In one type of embodiment, the base of the central post 26 interfaces (e.g., adheres) with the conducting wire 13. The distal opening 14 is wide enough for the central post 26 to slide in and out of the elongate catheter body 10. Contraction of the umbrella tip 26 occurs when the central post 26 is extended out of the elongate catheter body 10. Expansion of the umbrella tip 26 occurs when the central post 26 is extended into the elongate catheter body 10.

Extension or retraction of the umbrella tip body 26 is manipulated through the handle 11. In preferred embodiments, the handle 11 connects with the conducting wire 13 and steering spring 15. The conducting wire 13 attaches onto a lever 22 inside the handle 11. Extension of the lever 22 causes the central post 26 to extend outside of the elongate catheter body 10. As the central post 26 extends outside the elongate catheter body 10, the outer arms 27 reduce the degree of flexion. Retraction of the lever 22 causes the central post 26 to withdraw inside the elongate catheter body 10. As the central post 26 withdraws into the elongate catheter body 10, the outer arms 27 increase the degree of flexion.

An umbrella tip catheter may utilize numerous alternative steering embodiments, some of which are described above in relation to wire tip ablation catheters.

The terminus of the conducting wire attaches to an energy source cable 23 which establishes a connection with the energy source 16.

The proximal origin of the conducting wire 13 may be located at the distal end of the handle 11. At the proximal origin of the conducting wire 13, the conducting wire 13 is connected with an energy source 16. Embodiments of the present invention may utilize numerous forms of energy (e.g., radio-frequency energy, ultrasound, laser, liquid nitrogen, saline-mediated).

In preferred embodiments, radio-frequency energy is utilized as the energy source 16. Various radio-frequency energy generators are commercially available. A large (20×10 cm) ground patch is attached to the patient's back to complete the circuit. The current travels from the tip of the heart to the patch. The amount of energy utilized may be controlled by adjusting the power output of the energy source 16. Four parameters may be regulated through the energy source 16: power output, impedance, temperature, and duration of energy application.

The precise pattern of conductive elements assorted on an umbrella tip 26, along with the varying degrees of central post 26 expansion or contraction, permits a unique type of ablation lesion ranging from long and thin to large and deep in shape.

Alternative Embodiments

The present invention is not limited to wire tip or umbrella tip embodiments. It is contemplated that fragmented ablation lesions may be created with alternative designs. For example, zig-zag distal bodies, cross-hatch patterns, or other shapes may be utilized so long as the ablation lesion that is created is effective in prevention propagation electrical impulses.

Uses

The multifunctional catheter of the present invention has many advantages over the prior art. The heart has four chambers, or areas. During each heartbeat, the two uppers chambers (atria) contract, followed by the two lower chambers (ventricles). A heart beats in a constant rhythm—about 60 to 100 times per minute at rest. This action is directed by the heart's electrical system. An electrical impulse begins in an area called the sinus node, located in the upper part of the right atrium. When the sinus node fires, an impulse of electrical activity spreads through the right and left atria causing them to contract, forcing blood into the ventricles. Then the electrical impulses travel in an orderly manner to another area called the atrioventricular (AV) node and HIS-Purkinje network. The AV node is the electrical bridge that allows the impulse to go from the atria to the ventricles. The HIS-Purkinje network carries the impulses throughout the ventricles. The impulse then travels through the walls of the ventricle, causing them to contract. This forces blood out of the heart to the lungs and the body. Each electrical circuit has a wavelength. The wavelength is equivalent to the product of the impulse's conduction velocity and the impulse's effective refractory period.

Atrial fibrillation is the most common type of irregular heartbeat. In atrial fribrillation, an electrical impulse does not travel in an orderly fashion through the atria. Instead, many impulses begin and spread through the atria and compete for a chance to travel through the AV node. Such aberrant electrical impulses may originate from tissues other than the heart's electrical system.

One method of treatment for atrial fibrillation is ablation therapy. It is estimated that for initiation of atrial fibrillation, premature depolarizations from any cardiac structure is necessary. However, for perpetuation of atrial fibrillation both a continuous/continual surge of premature depolarizations and an atrial substrate capable of maintaining multiple reentrant circuits of atrial fibrillation are necessary. The goal of ablation therapy is to eliminate the premature depolarizations that trigger atrial fibrillation, and also to modify the atrial tissue such that the minimum wavelength of a reentrant electrical circuit will not be able to fit into the atrial tissue.

Procedurally, to eliminate triggers, a specific and localized area of interest (e.g., area of pulmonary vein connecting with atria, alternate group of cells emitting electrical impulses on their own) is targeted. A catheter with an ablation instrument is directed through a major vein or artery to the targeted location in the left atrium. Through the ablation instrument, radio-frequency is released onto the targeted location. A resulting scar or lesion is created. To modify the atrial substrate "maze" patterns of ablation lesions are created. The intent is to create continuous lesions without any connecting gaps.

The major shortcoming of present ablation techniques is an inability to avoid gaps in the maze ablation process. The heart walls have extremely complex curvatures making the creation of a continuous ablation maze nearly impossible. The typical result is an ablation maze containing numerous gaps. It is important to avoid the presence of gaps within the ablation maze because aberrant electrical impulses are able to propagate through them resulting in secondary arrhythmias. As such, gaps become reentrant circuits, and the atrial fibrillation is capable of continuing and different arrhythmias such as atrial flutter may also occur. In addition, creation of maze like lesions in atrium is extremely time consuming and is associated with a significant complication rate.

The present multifunctional catheter overcomes the gap problem faced in the prior art by not relying upon continuous lesions. The present invention creates spiral or umbrella shaped ablation lesions with very small gaps between the ablation lesions. Each gap is not large enough to allow an electrical impulse to propagate through it. The ablation tips of the present invention (e.g., wire tip or umbrella tip) have a relatively small surface area (e.g., 10-25 mm in diameter). In addition, the tips are pliable and soft, and yet have good support form the shaft. Thus, when the tip is pushed against the atrial wall, most, if not all, of the surface will form good contact without the risk of perforation as it is not a pointed catheter tip. Strategic placement of such ablation lesions essentially decreases the effective atrial mass that an aberrant electrical impulse may propagate through. This represents a significant improvement over the prior art because no longer will the laborious and often unsuccessful creation of ablation lesion mazes be necessary. It is also possible to use the ablation approach described in this disclosure in conjunction with ablation strategies that target elimination of triggers such as a pulmonary vein isolation procedure.

The present ablation catheters may be utilized in treating cardiac disorders including, but not limited to, atrial fibrillation, multifocal atrial tachycardia, inappropriate sinus tachycardia, atrial tachycardia, ventricular tachycardia, ventricular tachycardia, and WPW. In addition, the present ablation catheter may be utilized in several other medical treatments (e.g., ablation of solid tumors, destruction of tissues, assistance in surgical procedures, kidney stone removal).

All publications and patents mentioned in the above specification are herein incorporated by reference. Various modifications and variations of the described devices, compositions, methods, systems, and kits of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in art are intended to be within the scope of the following claims.

We claim:

1. A device comprising:
    an elongate catheter body comprising a proximal end and a distal end; and
    an umbrella tip body mounted at the distal end of the elongate catheter body, the umbrella tip body being movable between an expanded configuration and a contracted configuration, the umbrella tip body comprising:
    a central post extending from the distal end of the elongate catheter body and comprising a top portion; and
    a plurality of outer arms connected to the top portion of the central post, each of the plurality of outer arms comprising a first portion connected to a second portion at a hinge, the first portion comprising at least two sets of at least two conductive elements, wherein the at least two sets are separated by a first gap distance and the at least two conductive elements are separated by a second gap distance smaller than the first gap distance, the at least two sets being substantially coplanar in the expanded configuration; and
    wherein the umbrella tip body is configured to contact a tissue region and produce a shaped ablation lesion within the tissue region.

2. The device of claim 1, wherein said conductive elements comprise at least one conductive plate measuring 2-20 millimeters in size.

3. The device of claim 1, wherein said umbrella tip is configured to create radial lesions in body tissue.

4. The device of claim 1, further comprising a handle; wherein said handle is attached to said proximal end of said elongate catheter body.

5. The device of claim 4, wherein said handle is configured to move said umbrella tip body between the expanded and contracted configurations.

6. The device of claim 1, wherein said device further comprises an energy source configured to permit emission of energy from said umbrella tip body.

7. The device of claim 1, wherein the umbrella tip body defines a surface area between 10 and 25 square mm.

8. The device of claim 1, wherein the central post is hollow.

9. The device of claim 8 further comprising energy carrying conduits which pass through the central post.

10. The device of claim 1, wherein the central post is constructed of non-conductive material.

11. The device of claim 10, wherein the non-conductive material is selected from the group consisting of: polyurethane; plastic; polyethylene; and combinations thereof.

12. The device of claim 1, wherein the central post length is between 0.1 and 100 mm long.

13. The device of claim 1, wherein the central post has a diameter between 0.001 and 100 mm.

14. The device of claim 1, wherein the central post has the geometry of a cylindrical rod.

15. The device of claim 1, wherein the elongate catheter body includes a lumen from the proximal end to the distal end, and the central post can be retracted to be located with said lumen.

16. The device of claim 1, wherein the umbrella tip body includes between 2 and 5 outer arms.

17. The device of claim 1, wherein the distance between a first outer arm and another outer arm is different than the distance between a second outer arm and another outer arm.

18. The device of claim 1, wherein the distance between each sequential outer arm is substantially equal.

19. The device of claim 1, wherein at least one outer arm is constructed of non-conductive materials.

20. The device of claim 19 wherein at least one outer arm is constructed of materials selected from the group consisting of: polyurethane; polyethylene; and combinations thereof.

21. The device of claim 1, wherein at least one outer arm has a length between 0.1 and 100 mm.

22. The device of claim 1, wherein the umbrella tip body defines a surface area between 0.03 square millimeters and 314 square centimeters.

23. The device of claim 1, wherein at least one outer arm has a diameter greater than about 0.001 millimeters.

24. The device of claim 1, wherein at least one outer arm further includes a thermal monitoring circuit component along its length.

25. The device of claim 24, wherein the thermal monitoring circuit is used to detect and maintain temperatures during tissue ablation.

26. The device of claim 1, wherein at least one outer arm is flexible.

27. The device of claim 1, wherein at least one outer arm is rigid.

28. The device of claim 1, wherein the hinge is near the midpoint of each of said plurality of outer arms.

29. The device of claim 1, wherein the hinge allows one hundred and eighty degrees of flexion.

30. The device of claim 1, wherein said device is configured such that a lesion shape is determined by one or more of: a configuration of conductive elements on the umbrella tip; a selection of conductive elements to be energized; an amount of umbrella expansion and/or contraction; and combinations thereof.

31. The device of claim 1, wherein the at least one conductive element is an electrode.

32. The device of claim 1, wherein the at least one conductive element releases energy.

33. The device of claim 1, wherein the first gap distance is between 0.1 and 100 mm.

34. The device of claim 1, wherein each of the plurality of outer arms includes a first conductive element, a second conductive element and a third conductive element, and wherein the first and second conductive elements are separated by a distance less than the distance separating the second and third conductive elements.

35. The device of claim 1, wherein the at least one conductive element is pressure fit to the outer arm.

36. The device of claim 1, wherein the at least one conductive element is soldered and swaged to the outer arm.

37. The device of claim 1, wherein the at least one conductive element is mechanically fixed to the outer arm with an adhesive.

38. The device of claim 1, wherein the at least one conductive element ranges in size from 0.1 to 20 mm.

39. The device of claim 1, wherein at least one of the plurality of outer arms includes at least three conductive elements fixedly attached to said outer arm in a staggered pattern.

40. The device of claim 1, wherein each of the at least two sets of conducting elements includes the same number of conductive elements.

41. The device of claim 40, wherein at least one set is limited to a single coil.

42. The device of claim 1, wherein each of the at least two sets of conducting elements includes different numbers of conductive elements.

43. The device of claim 42 wherein at least one set is limited to a single coil.

44. The device of claim 1, wherein a first outer arm includes one pattern of one or more conductive elements and a second outer arm includes a different pattern of conductive elements.

45. The device of claim 1, wherein the conductive element comprises a continuous ring of densely wound wire.

46. The device of claim 45, wherein the wire is constructed of materials selected from the group consisting of: silver; copper; platinum; and combinations thereof.

47. The device of claim 45, wherein the continuous ring is constructed of: densely wound copper wire; densely wound platinum wire; loosely wound silver wire; and combinations thereof.

48. The device of claim 1, wherein the conductive element comprises a conductive plate.

49. The device of claim 1, wherein the conductive element comprises a solid ring of conductive material.

50. The device of claim 1, wherein the conductive element is constructed of materials selected from the group consisting of: copper; silver; platinum; and combinations thereof.

51. The device of claim 1, comprising multiple conductive elements and at least two of said conductive elements are conductive plates with different lengths.

52. The device of claim 48, comprising two conductive plates, wherein a first conductive plate is fixedly mounted to a first outer arm and a second conductive plate is fixedly mounted to a second outer arm.

53. The device of claim 52, wherein the first conductive plate is mounted near the distal end of the first outer arm.

54. The device of claim 1, comprising multiple conductive elements including both conductive plates and conductive coils.

55. The device of claim 1, wherein said device is configured to create a series of elongate lesions with small or no gaps in between at least two lesions.

56. The device of claim 1, wherein said device is configured to creates lesions ranging from long and thin to large and deep.

57. The device of claim 1, wherein said device is configured to allow manipulation of the umbrella tip to create varied patterns of lesions.

58. The device of claim 1, wherein said device is configured to allow an operator to create a maze of lesions.

59. The device of claim 1, wherein said device is configured to create lesions to provide treatment for one or more of: atrial fibrillation; multifocal atrial tachycardia; inappropriate sinus tachycardia; atrial tachycardia; ventricular tachycardia; ventricular tachycardia; Wolff-Parkinson-White Syndrome; and supraventricular tachycardia.

60. The device of claim 1, wherein said device is configured to create lesions located in one or more of: heart; prostate; brain; gall bladder; and uterus.

61. The device of claim 1, further comprising an energy source.

62. The device of claim 61, wherein the energy source provides energy selected from the group consisting of: microwave energy; cryoenergy; ultrasound energy; ultrasound energy; radiofrequency energy; and combinations thereof.

63. The device of claim 61, wherein the energy source provides radiofrequency energy, said device configured to regulate parameters selected from the group consisting of: power output; impedance; temperature; duration of energy application; and combinations thereof.

64. The device of claim 1, further comprising a thermal monitoring circuit.

65. The device of claim 64, wherein the thermal monitoring circuit comprises a plurality of circuits joined in series.

66. The device of claim 64, further comprising at least one conductive element configured to deliver energy to ablate the tissue, wherein the thermal monitoring circuit is thermally coupled to said at least one conductive element.

* * * * *